(12) United States Patent
Kiehne

(10) Patent No.: US 6,629,985 B1
(45) Date of Patent: *Oct. 7, 2003

(54) SURGICAL SCALPEL WITH RETRACTABLE GUARD

(75) Inventor: Vanessa Gay Kiehne, Springwood (AU)

(73) Assignee: Occupational & Medical Innovations PTY LTD, Springwood (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/786,363

(22) PCT Filed: Mar. 9, 2000

(86) PCT No.: PCT/AU00/00166

§ 371 (c)(1),
(2), (4) Date: Mar. 21, 2001

(87) PCT Pub. No.: WO01/05312

PCT Pub. Date: Jan. 25, 2001

(30) Foreign Application Priority Data

Jul. 15, 1999 (AU) .................................................. 40144

(51) Int. Cl.[7] ............................. A61B 17/32; B26B 1/08
(52) U.S. Cl. ............................. 606/167; 30/162; 30/339
(58) Field of Search .................................. 606/167, 170, 606/181; 30/2, 335, 156, 157, 151, 162; 206/352, 356, 349

(56) References Cited

U.S. PATENT DOCUMENTS

| 3,171,201 A | * | 3/1965 | Carifi ........................... 30/162 |
| 4,106,620 A | * | 8/1978 | Brimmer et al. ............. 206/356 |
| 4,922,614 A | * | 5/1990 | Machida ....................... 30/339 |
| 5,475,925 A | * | 12/1995 | Newman et al. .............. 30/162 |
| 5,527,329 A | | 6/1996 | Gharibian |
| 5,792,162 A | | 8/1998 | Jolly et al. |
| 5,827,309 A | | 10/1998 | Jolly et al. |
| 5,868,771 A | | 2/1999 | Herbert et al. |
| 5,919,201 A | | 7/1999 | Carter et al. |
| 5,938,675 A | | 8/1999 | Gharibian |
| 5,941,892 A | | 8/1999 | Cohn et al. |
| 6,015,419 A | | 1/2000 | Strome et al. |
| 6,022,364 A | * | 2/2000 | Flumene et al. ............. 606/166 |
| 6,216,868 B1 | * | 4/2001 | Rastegar et al. ............ 206/356 |
| 6,254,621 B1 | * | 7/2001 | Shackelford et al. ....... 606/167 |

FOREIGN PATENT DOCUMENTS

| WO | WO 95/15723 | 6/1995 |

* cited by examiner

*Primary Examiner*—Ismael Izaguirre
(74) *Attorney, Agent, or Firm*—Hoffmann, Wasson & Gitler, PC

(57) ABSTRACT

A safety scalpel blade assembly comprising a scalpel blade, a guard which extends at least about the cutting edge of the blade, and releasable attachments device which releasably attach the blade to the guard as the assembly is being attached to the scalpel handle, thereby preventing the blade from cutting a person, but which releases the blade from the guard when the blade is attached to the blade carrier of the scalpel handle.

12 Claims, 6 Drawing Sheets

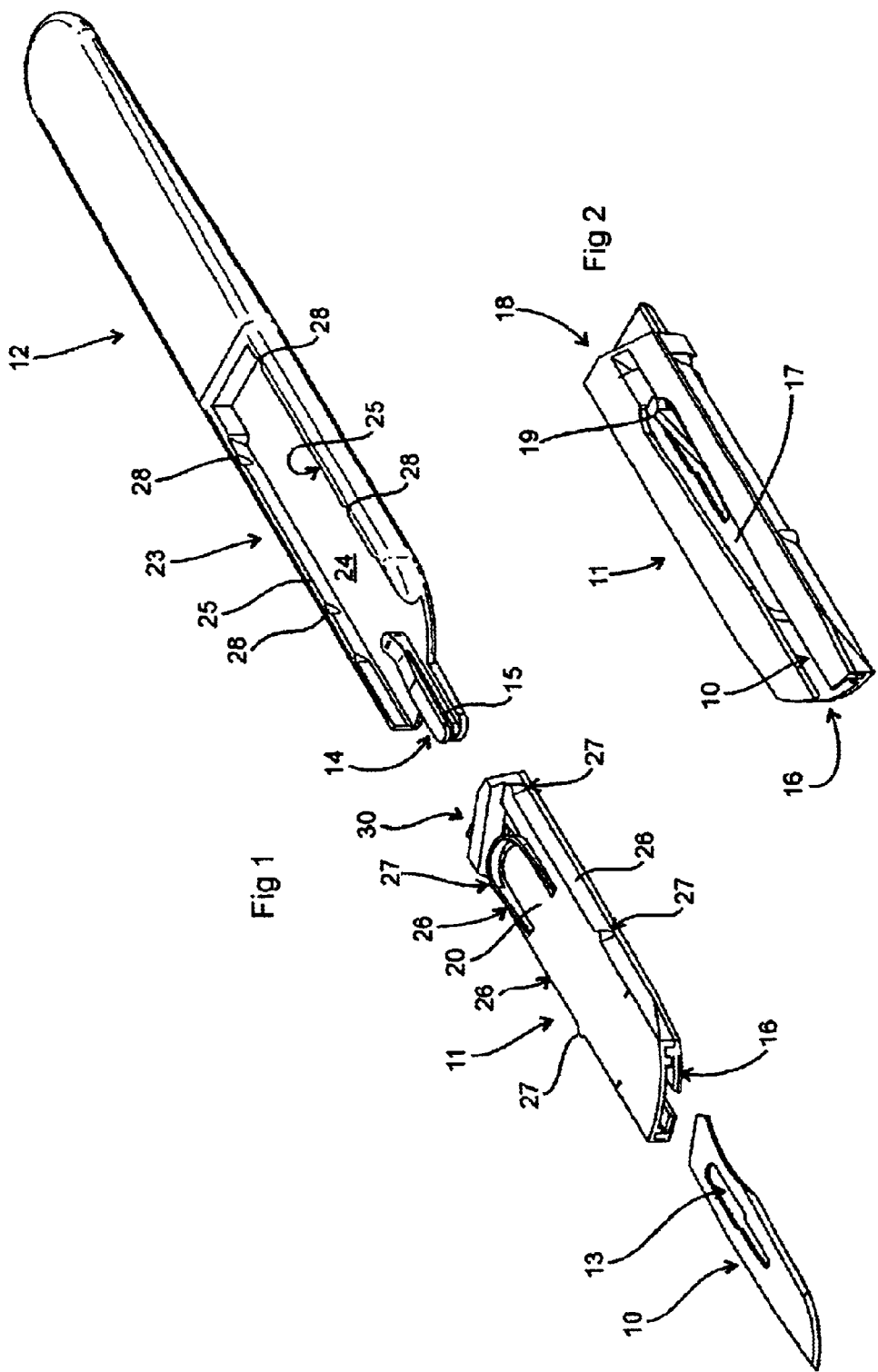

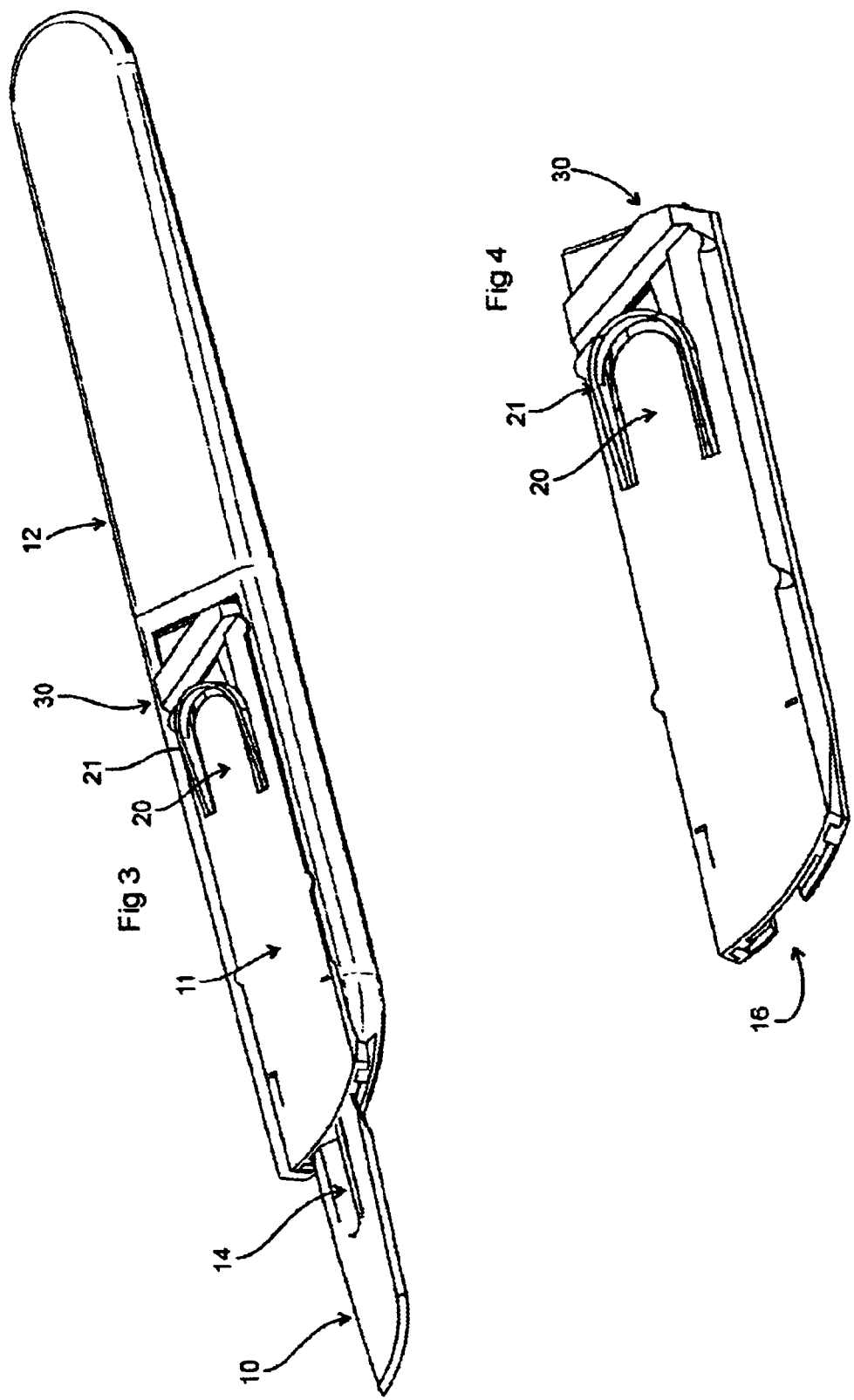

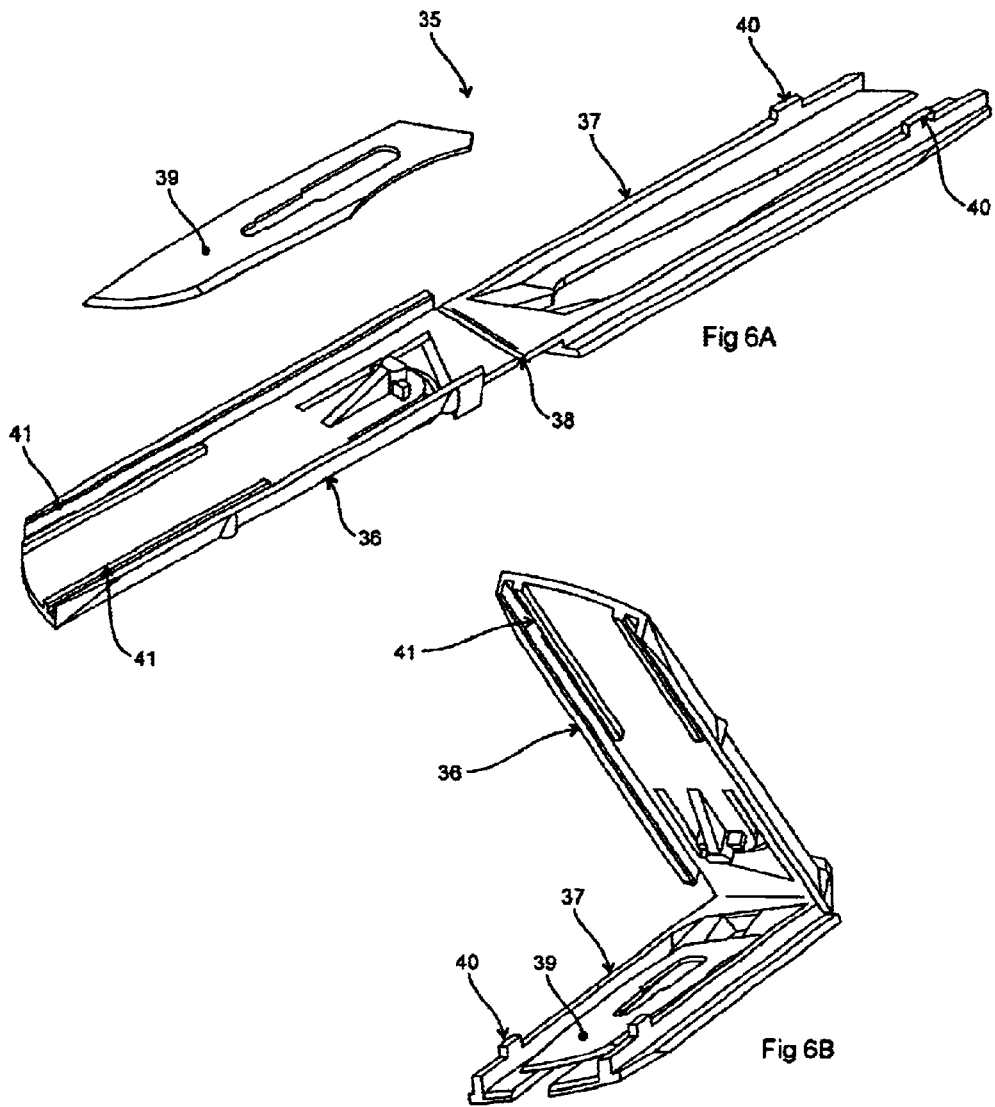

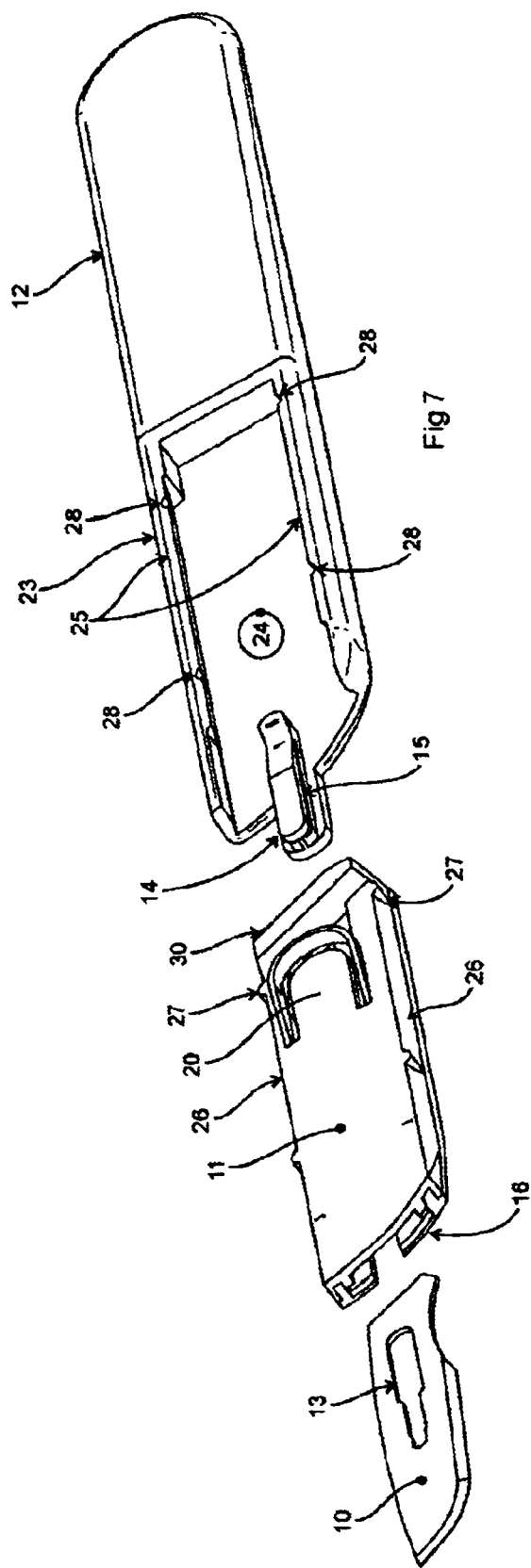
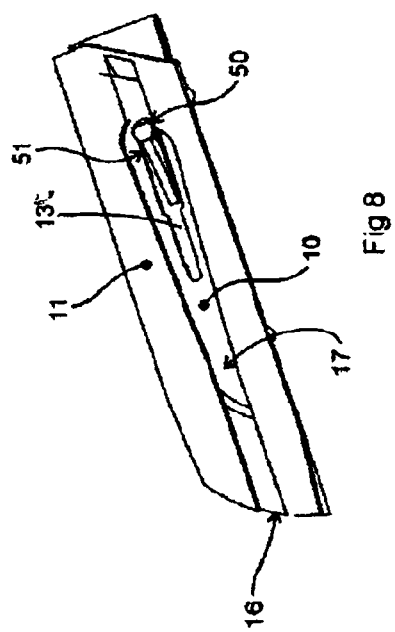

SURGICAL SCALPEL WITH RETRACTABLE GUARD

FIELD OF THE INVENTION

This invention relates to a surgical scalpel which has a retractable guard to reduce the incidence of sharps injury.

The invention will be described with reference to a surgical scalpel but it should be appreciated that the invention can be construed broadly enough to cover any other type of cutting implement which requires safe handling procedures.

BACKGROUND ART

Surgical scalpels or surgical knives which are in commercial use have a handle and a disposable blade. The blade can be detached from the handle and disposed of by deposit in a special container which can thereafter be handled with reduced hazard of sharps injury.

A sharps injury means any cutting or penetrating object that can be reasonably anticipated to penetrate the skin or other part of the body to result in an exposure incident which includes occupational exposure to blood and other potentially infectious materials. Clearly, this covers scalpels and other types of surgical knives.

The commercially available scalpels which have a disposable blade generally have reusable handles. The handle can be sterilised by autoclaving and reused, and these handles are usually formed from metal. The surgical blade comes packaged in a protective foil. The foil is carefully opened to expose the blade. The blade is then held between thumb and finger and carefully attached to an extending projection of finger on the handle. Upon completion of the surgical procedure, the blade is either manually detached from the handle and placed in a sharps bin, or the handle with the blade is inserted into a container which breaks off the blade.

It can be seen that attachment of the blade to the handle is a hazardous procedure and can easily result in a sharps injury. If the blade is manually detached, this can also result in a sharps injury which is even more hazardous as the blade may be contaminated.

During surgical use, the scalpels can accidentally cut the surgeon's fingers, or the fingers of nurses and other support persons in the operating theatre. As well, operating personnel can be accidentally cut when the scalpel is passed between personnel.

To partially mitigate against accidental sharps injuries in handling the scalpel, it is known to provide a retractable blade guard. The blade guard is attached to the handle, and can be manually pushed between an extended blade guarding position, and a retracted blade exposed position. Thus, blade guards attached to scalpel handles are known.

These blade guards have some disadvantages. Firstly, by being part of the handle, the handle must be thoroughly cleaned from any blood and tissue after use, if the handle is to be reused. The blade guard can catch and contain tissue, congealed blood, and the like in the various nooks and cavities in the blade guard and it is extremely difficult to ensure that the blade guard is absolutely spotlessly clean to allow the handle with the attached blade guard to be reused. To allow the handle to be reused many times, the blade guard must be fairly robust and this can result in the guard being of fairly complex manufacture, quite bulky, and quite expensive.

A second disadvantage with this arrangement is that the blade guard cannot protect against initial attachment of the sterile blade to the handle. That is, the blade guard must be fully retracted to expose the projection or finger on the handle to which the blade is attached. The blade must be attached in the usual manner which is to initially remove it from its protective foil and then physically attach it to the handle. Thus, existing blade guards do not reduce or eliminate sharps injuries which can result in initial attachment of the blade. As well, these guards do not protect against removal of the blade from the handle.

OBJECT OF THE INVENTION

The present invention is directed to an assembly which contains a blade attached to a blade guard. The assembly can be packaged within a sterile foil (similar to conventional blades). The assembly can be removed from the foil and can be safely handled with little risk of the blade cutting the person, and the assembly can be attached to a scalpel handle with the blade guard in place. When the assembly is attached to the scalpel handle, the blade guard can then be retracted fully or partially to expose the blade. When the surgical procedure is finished, the blade guard can be pushed back over the blade and the blade and blade guard can be removed from the handle for safe disposal. In this arrangement, the handle itself does not keep the blade guard as the guard is disposed with the blade after use.

With this arrangement, there is reduced likelihood of sharps injuries in attachment of a blade to the handle. As well, the handle does not keep the guard which means that the handle can be more easily cleaned and sterilised for reuse. The guard can stay with the blade when the blade is removed which reduces the incidence of sharps injury when removing the blade from the handle.

It is an object of the invention to provide a scalpel blade assembly, and a scalpel which may at least partially overcome the abovementioned disadvantages or provide the public with a useful or commercial choice.

In one form, the invention resides in a safety scalpel blade assembly comprising a scalpel blade, a guard which extends at least about the cutting edge of the blade, and releasable attachment means to releasably attach the blade to the guard, the attachment means being operable between a locking position where the blade is held relative to the guard such that the cutting edge is protected by the guard, and a free position where the blade can slide out of the guard.

In a more particularised form, the invention comprises a safety scalpel blade assembly which is able to be attached to a handle of the type which has a blade carrier in the form of a finger, the assembly comprising a scalpel blade which can be of conventional manufacture and which has a slot which allows the blade to be attached to the blade carrier on the handle, and a guard which extends at least about the cutting edge of the blade, the guard having attachment means which locks the blade to the guard as the assembly is being attached to the handle thereby preventing the blade from cutting a person, but which releases the blade from the guard when the blade is attached to the blade carrier on the handle.

In another form, the invention resides in a scalpel comprising a scalpel blade assembly and a handle, the scalpel blade assembly having:

a scalpel blade, a guard which extends at least about the cutting edge of the blade, and releasable attachment means to releasably attach the blade to the guard, the attachment means being operable between a locking position where the blade is held relative to the guard such that the cutting edge is protected by the guard, and a free position where the blade can slide out of the guard, the handle having:
a portion which is releasably lockable to the blade, the handle further having guide means which engages with the guard when the handle is attached to the blade to allow the guard to slide along the guide means on the handle between a retracted position where at least a portion of the cutting edge of the blade is exposed, and an extended position where the cutting edge of the blade is protected,
the scalpel further having means to move the attachment means to its free position when the handle is attached to the blade.

The scalpel blade assembly has the scalpel blade initially attached to a blade guard. The assembly can be packed in a sterile foil and the foil can be opened to safely remove the blade and the blade guard. The assembly can then be attached to a scalpel handle and thereafter the guard can be retracted to expose the scalpel blade.

The scalpel blade can be of various types depending on the surgical procedure to be carried out. It is usual for the blade to be elongate and to have a forward cutting edge. The blade body is provided with an elongate slot extending therethrough and the slot allows the blade to be attached to a projection or finger on the handle. This arrangement is entirely conventional. The invention is envisaged to cover surgical devices which may be other than a blade but which also are attachable to a handle and which require safe handling procedures.

The guard extends at least about the cutting edge of the blade to protect against sharps injury. The guard may be formed from plastics material although other materials are envisaged. As the blade assembly is disposed of after use, it is preferred that the guard is made of fairly inexpensive material which is however still suited for use and which can be sterilised.

The guard can extend substantially around the blade to form a shroud or sleeve. The forward end of the guard (that is the end where the front of the blade sits) should be open or have a passageway to allow the blade to extend from the guard. To facilitate attachment of the blade/guard assembly to the handle, the guard may be required to have an opening or slot to allow the handle to be attached to the blade while the guard is still in place, and to allow the guard to be retracted from the blade when the blade is attached to the handle.

The assembly has a releasable attachment means. The releasable attachment means functions to initially attach the blade to the guard such that when the blade/guard assembly is removed from its protective package, the blade does not inadvertently fall out of the guard or expose a cutting edge. The attachment means can also function to hold the blade in the guard when the blade is removed for disposal. In one form, this can be achieved by a projection or button on the guard which extends into the slot in the blade body (the slot being where the handle attaches to the blade). The projection or button therefore prevents the blade from inadvertently sliding out of the guard and presenting a cutting edge.

If desired, the guard may be provided with a further projection, or fin which extends into the slot in the blade and can function to prevent the blade from "rattling" in the guard.

The releasable attachment means may also be slightly biased, inter alia to push the blade against a wall of the guard again to prevent the blade from rattling or exhibiting undesired movement in the guard.

The blade assembly can be attached to a scalpel or knife handle. The knife handle can have a forward projection or finger which has a profile to allow it to releasably lock to the slot in the blade. This arrangement is known in the art. The handle can be provided with means to release the blade from the guard when the handle is attached to the blade. In one form, the projection or finger on the handle can have a profile such that when it attaches to the blade, it also releases the blade from the guard thereby allowing the guard to be retracted to expose the blade.

The handle is provided with guide means to engage with the guard and to allow the guard to slide between retracted and extended positions. The guide means can be in the form of a recess in the handle in which the guide slides.

The guard can be retracted from the blade to expose various lengths of the blade. For instance, means may be provided to allow the guard to be releasably locked or held in various retracted positions to expose various lengths of the blade. This allows the cutting depth of the blade to be adjusted, and can also ensure that only a necessary amount of blade is exposed with the remainder of the blade still being protected by the guard, the purpose being to further minimise accidental injury.

BRIEF DESCRIPTION OF THE DRAWINGS

Embodiments of the invention will be described with reference to the following figures in which FIG. 1 is an exploded view of a scalpel showing the scalpel blade, the blade guard, and the scalpel handle.

FIG. 2 shows the scalpel blade assembly with the blade initially held within the guard.

FIG. 3 shows the blade attached to the handle with the guard in the retracted position exposing the blade.

FIG. 4 is an enlarged view of the blade guard illustrated in FIG. 1.

FIGS. 6A–6B illustrate a mouldable blade guard.

FIGS. 7–13 illustrate a guard according to a second embodiment.

BEST MODE

Figure 5A:
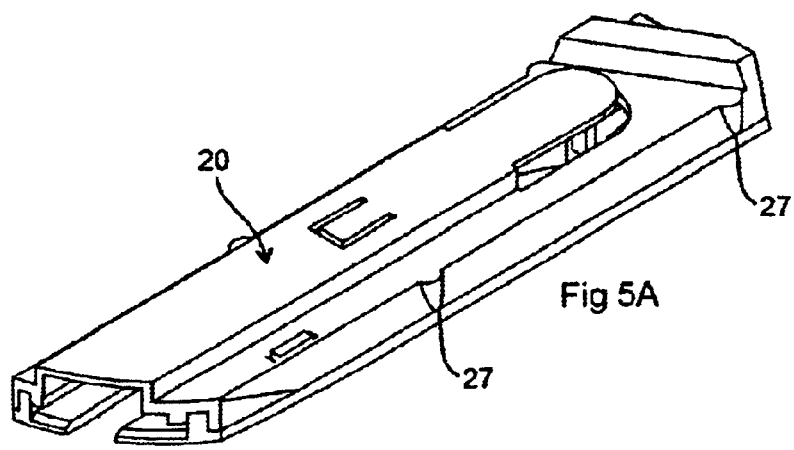
FIGS. 5A–5C show top, bottom and section views of a blade guard according to an alternative embodiment.

Referring to FIGS. 1 and 7, there are illustrated two versions of a scalpel which consist of three main components being a scalpel blade 10, a blade guard 11, and a scalpel handle 12. Blade 10 is of conventional design and is widely available in the marketplace. The blade is formed of stainless steel, has a forward cutting edge, and is provided with an elongate profiled slot 13 which is again entirely conventional. Handle 12 has a forwardly extending projection or finger 14 which is profiled and has opposed side recesses or grooves 15 (only one groove illustrated). Blade 10 is attached to finger 14 with the internal edges of slot 13 sliding along grooves 15. This is again conventional in the art.

FIG. 1 illustrates guard 11 which functions to cover or protect the cutting edge of blade 10 as the blade is attached. That is, blade 10 can be attached with guard 11 in place such that at no stage does a person's hand contact the cutting edge of the blade as the blade is attached to finger 14.

FIGS. 2 and 8 illustrate two versions of a scalpel blade assembly which consist of blade 10 and guard 11 with blade 10 now being entirely within guard 11. Guard 11 in FIGS. 2 and 8 is the same as guard 11 in FIGS. 1 and 7 except FIGS. 2 and 8 are inverted views of the guard of FIGS. 1 and 7.

Guard 11 can be formed from relatively inexpensive plastic material and is preferably clear or at least translucent such that that the blade can be seen through the guard. The guard substantially encompasses the blade to form a shroud or sleeve. The front 16 of the guard is open such that the guard can be retracted to expose blade 10. One side wall of guard 11 is provided with an elongate slot 17 which extends entirely along the side wall from the front 16 to the rear wall 18 of the guard. The function of slot 17 is to allow the passing of the finger therethrough and not interfere with retraction of the guard when blade 10 is attached to finger 14.

Figure 5B:
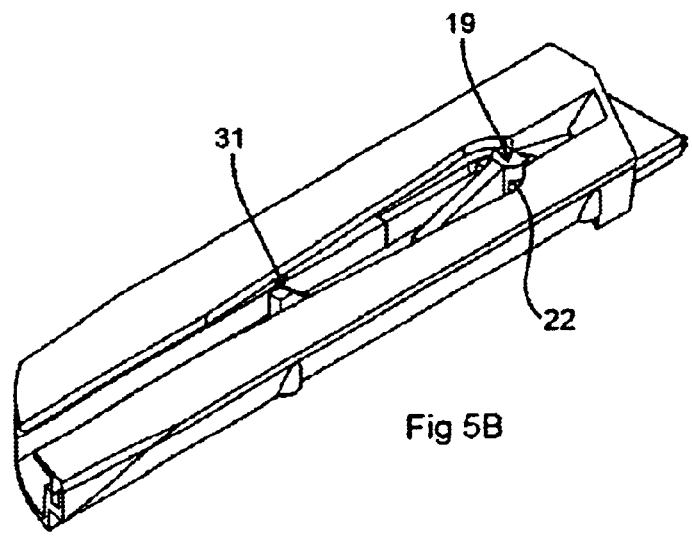
Figure 5C:
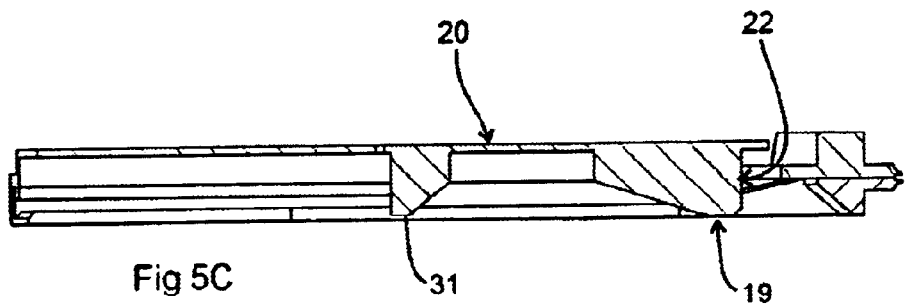

Guard 11 has a releasable attachment means which functions to hold blade 10 in guard 11 (see FIGS. 2 and 8) before the blade/guard assembly is attached to scalpel handle 12. In the embodiment of FIG. 2, the releasable attachment means is in the form of a projection or button 19 which is also illustrated in FIG. 5C. Button 19 sits at one end of a flat finger 20 (see FIG. 1). Finger 20 is integrally formed with the remainder of guard 11 and is able to be depressed by virtue of its finger-like quality.

A protective raised wall 21 extends around finger 20 but finger 20 is not attached to wall 21 which means that finger 20 can pivot or be depressed within the confines of wall 21. Wall 21 functions inter alia to protect the rather small finger against unintentional movement, or damage.

In the embodiment of FIGS. 7 and 8, the raised wall is not present. The projection 50 (see also FIG. 12) has a ramped wall 51 extending from finger 20.

In use, the scalpel blade assembly as illustrated in FIGS. 2 and 8 is assembled and can be placed in a foil package in a manner similar to current scalpel blades. The assembly can be removed from a foil package and it can be seen from FIGS. 2 and 8 that button 19, 50 holds the blade within guard 11 and therefore the assembly can be picked up by the guard 11 which means that there is little or no likelihood of the blade causing a stick injury.

The assembly can then be placed onto finger 14 with finger 14 passing into slot 13 to attach the blade to finger 14. Finger 14 is profiled such that when it extends into slot 13, it also pushes away button 19, 50 against the bias of finger 20. This in turn releases blade 10 from its housing 11. For as long as blade 10 is attached to finger 14, the profile of finger 14 keeps button 19, 50 out of slot 13 and therefore prevents button 19, 50 from re-engaging with the blade. Upon removal of the blade and guard assembly, the guard is first pushed to the forward position where it covers the blade and then the blade is decoupled from finger 14. As soon as this occurs, button 19, 50 is released and the with bias of finger 20 will re-enter into slot 13 to again hold the blade within the guard. The blade and guard assembly can now be safely disposed of in a sharps bin with little or no likelihood of stick injury resulting.

Figure 12:
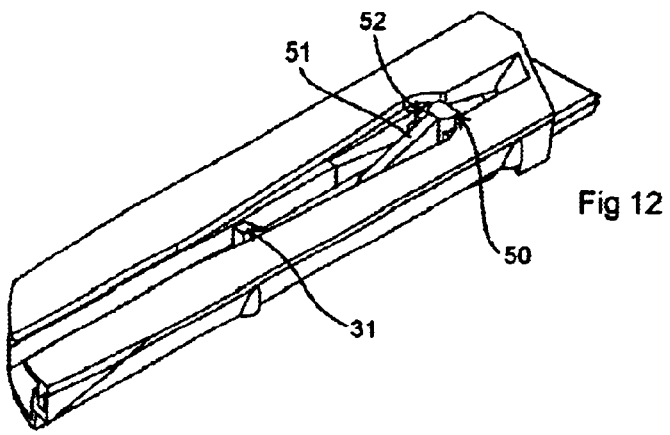
Figure 13:
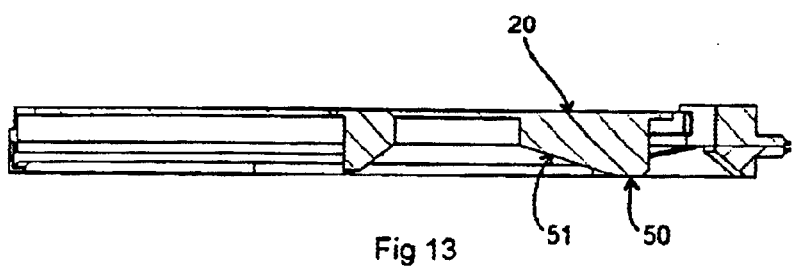

Finger 20 is biased to bias button 19, 50 into slot 13. In FIG. 2, button 19 extends from a larger shoulder portion 22 (more clearly illustrated in FIGS. 5B and 5C). Should portion 22 is too large to extend through slot 13 but instead abuts against one side of the blade. With the biasing action of finger 20, shoulder portion 22 functions to gently push the blade against one side wall of guard 11 and prevents the blade from rattling or from exhibiting unintentional movement. The position of button 19 is such that when blade 10 is within guard 11 (see FIG. 2), the button is adjacent the rear portion of slot 13. This prevents the blade from further extension out of the guard. Movement of the blade in the other direction is prevented as rear end 18 of guard 11 does not have an open end as does the front 16. Thus, blade 10 is essentially trapped within housing 11 until such time as the assembly is attached to finger 14 which in turn pushes button 19 out of engagement with slot 13. In FIGS. 8, 12 and 13, button 50 has opposed shoulder portions 52 which serve the same function as shoulder portion 22 in FIG. 2.

Figure 9:
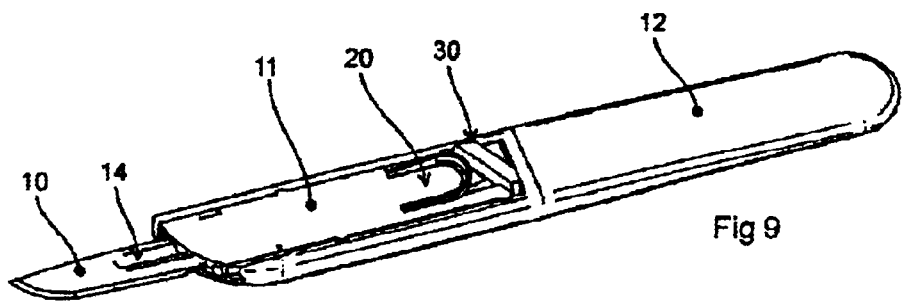
Figure 10:
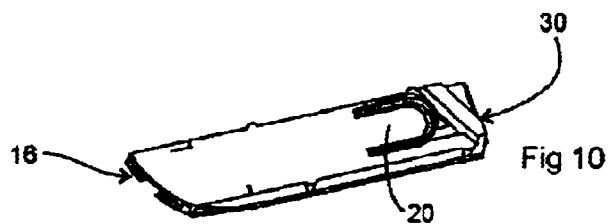
Figure 11:
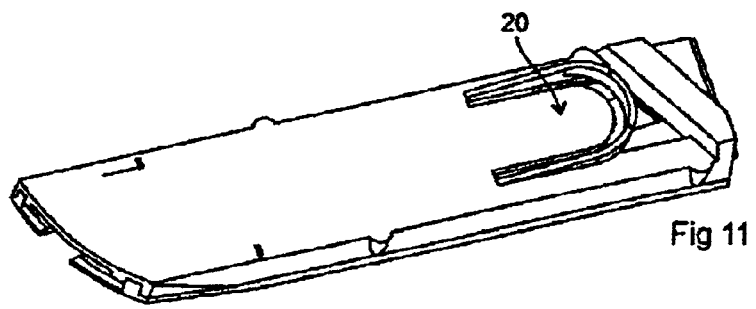

Handle 12 has a guide means 23 which in the embodiment is in the form of a recess 24 on the forward portion of handle 12 and immediately behind finger 14. The recess is sufficiently long such that guard 11 can be pulled back to fully expose blade 10. This fully retracted blade exposing position is illustrated in FIGS. 3 and 9. The recess 24, which forms part of the guide means in handle 12, is configured to accept the shape of guard 11. Recess 24 has opposed side walls 25 which guide the opposed side walls 26 of guard 11.

Guard 11 has a number of small projections or buttons 27 extending from each side wall 26, and the side walls 25 of recess 24 have corresponding recesses 28. The function of buttons 27 and recesses 28 is to allow the guard 11 to be retracted along recess 24 and be releasably locked into preset positions where an opposed pair of buttons 27 click into an opposed pair of recesses 28. The releasable locking arrangement is such that the surgeon's thumb is able to slide the guard to release the guard from engagement with the guide means. However, when the surgeon's thumb is not on guard 11, the guard is held in place sufficiently to prevent it from inadvertently becoming loose. This arrangement has the advantage that if only a small part of the cutting blade is required, the guard can be clicked into an only partially retracted position thereby still protecting the remainder of the cutting edge of the blade against stick injury. The guard can also provide a means to measure the depth of the cut by exposing only a certain length of the cutting blade.

The guard has a thumb engageable projection 30 such that a surgeon can grip the guard by projection 30 and can extend or retract the guard in a single simple motion. Raised wall 21 prevents the surgeon's thumb from accidentally pushing in finger 20.

FIGS. 5A–5C and FIGS. 11–13 show variations to the guard. In these variations, the guard has an additional fin 31 which sits in slot 13 of blade 10 and functions to keep the blade central. Fin 31 is also attached to finger 20 such that it is pushed out of the way when the blade is attached to the scalpel handle.

FIGS. 6A and 6B illustrate a blade guard 35 which is injection moulded and consists of two halves 36,37 connected via a hinge line 38. The guard is moulded in a flat configuration illustrated in FIG. 6A. The blade 39 (see FIG. 6B) is placed on one half 37 and the other half 36 is bent via hinge line 38 to overlie the first half 37. The halves are snap locked together by projections 40 on one of the halves which engage into recesses 41 on the other half.

It should be appreciated that various other changes and modifications can be made to the embodiment described without departing from the spirit and scope of the invention as claimed.

What is claimed is:

1. A safety scalpel blade assembly which is able to be attached to a handle of the type which has a blade carrier in the form of a finger, the assembly comprising a scalpel blade which can be of conventional manufacture and which has a profile slot which allows the blade to be attached to the blade carrier on the handle, and a guard which extends at least about the cutting edge of the blade, the guard having attachment means which locks the blade to the guard as the assembly is being attached to the handle thereby preventing the blade from cutting a person, but which releases the blade from the guard when the blade is attached to the blade carrier on the handle, wherein the guard has two opposed side walls defining a space therebetween in which the blade in situated, one said side wall having an elongate slot extending into and along the side wall, the elongate slot adapted to allow the blade carrier to pass through the elongate slot and into engagement with the profile slot in the scalpel blade to attach to the blade while the guard is still in place, and to allow the guard to be retracted from the blade when the blade is attached to the handle.

2. The assembly of claim 1, wherein the guard extends substantially around the blade to form a shroud or sleeve.

3. The assembly of claim 2, wherein the guard has an open front end which allows the blade to extend from the guard through the open front.

4. The assembly of claim 3, wherein the elongate slot extends through and along the side wall, the slot having one open end which communicates with the front end of the guard.

5. The assembly of claim 4, wherein the attachment means is a projection on the guard which is moveable between a first position where the projection prevents the blade from extending out of the guard and presenting a cutting edge, and a free position where the blade can at least partially extend from the guard.

6. The assembly of claim 5, wherein the projection extends at least partially into the slot in the blade to prevent the blade from inadvertently sliding out of the guard and presenting a cutting edge.

7. The assembly of claim 5, wherein the projection abuts against a portion of the blade, the projection being biased by a biasing means to bias the projection against the blade to push the blade against one said side wall of the guard.

8. The assembly of claim 1 which is packed in a sterile foil.

9. The assembly of claim 1, wherein the guard and the handle are provided with releasable attachment means to allow the guard to be held in the retracted position on the handle.

10. A knife comprising a handle of the type which has a blade carrier in the form of a finger, and a blade assembly which comprises a scalpel blade which has a profile slot which allows the blade to be attached to the blade carrier on the handle, and a guard which extends at least about the cutting edge of the blade, the guard having attachment means which locks the blade to the guard as the assembly is being attached to the handle thereby preventing the blade from cutting a person, but which releases the blade from the guard when the blade is attached to the blade carrier on the handle, wherein the guard has two opposed side walls defining a space therebetween in which the blade in situated, one said side wall having an elongate slot extending into and along the side wall, the elongate slot adapted to allow the blade carrier to pass through the elongate slot and into engagement with the profile slot in the scalpel blade to attach to the blade while the guard is still in place, and to allow the guard to be retracted from the blade when the blade is attached to the handle.

11. The knife of claim 10, wherein the finger on the handle has profile which moves the projection of the attachment means to the free position to release the blade from the guard when the finger is attached to the blade.

12. The knife of claim 11, wherein the handle is provided with guide means to engage with the guard and to allow the guard to slide between retracted and extended position, the guide means comprising a recess in the handle in which the guide slides.

* * * * *